United States Patent [19]

Sporkenbach et al.

[11] 4,404,191

[45] Sep. 13, 1983

[54] VIRUCIDAL METHOD

[75] Inventors: Jutta Sporkenbach; Heinz Eggensperger, both of Hamburg; Lothar Bücklers, Norderstedt; Helmut H. Ehlers, Hamburg; Ulrich Eigener, Henstedt-Ulzburg; Hans-Peter Harke, Hamburg, all of Fed. Rep. of Germany

[73] Assignee: Sterling Drug Inc., New York, N.Y.

[21] Appl. No.: 322,557

[22] Filed: Nov. 18, 1981

[30] Foreign Application Priority Data

Dec. 12, 1980 [DE] Fed. Rep. of Germany ....... 3046769

[51] Int. Cl.$^3$ ..................... A01N 59/00; A61K 33/40; A01N 59/02; A61K 33/04; A01N 65/00; A61K 33/00

[52] U.S. Cl. .................................. 424/130; 424/162; 424/164; 424/127

[58] Field of Search ............... 424/164, 162, 130, 128, 424/127; 252/106; 423/513

[56] References Cited

U.S. PATENT DOCUMENTS 3,873,696 3/1975 Randeri et al. ................. 424/162 X

OTHER PUBLICATIONS

Gleason et al., Clinical Toxicology of Commercial Products, Third Edition, (1969), p. 118.
The Merck Index, Ninth Edition, (1976), pp. 142, 143, 701, 702, 1111, 1113, 1121 and 1148.
L. B. al.; et al., American Journal of Clinical Pathology, vol. 33, No. 1, Jan. 1960, pp. 30-33.
cf. Horn, Privora, Weuffen: "Handbook of Disinfection and Sterilization", vol. III, (1974), 7-15.
J. Sporkenbach: "The Lack of Inactivation Activity of Some PVP-Iodine Compounds Toward Poliomyelitis and Adenoviruses", Hygiene & Medicine 7, 357-362, (1980).

Primary Examiner—Jerome D. Goldberg
Assistant Examiner—Freda Abramson
Attorney, Agent, or Firm—Frederik W. Stonner; Paul E. Dupont; B. Woodrow Wyatt

[57] ABSTRACT

A method is provided for inactivating viruses on animate and inanimate surfaces which comprises contacting the locus of said viruses with an antivirally effective amount of a salt of peroxymonosulfuric acid.

7 Claims, No Drawings

VIRUCIDAL METHOD

BACKGROUND OF THE INVENTION

1. Field of the Invention

The invention relates to a method and compositions for inactivating viruses on animate and inanimate surfaces in which the anti-virally effective agent is a salt of peroxymonosulfuric acid.

2. Description of the Prior Art

It is known that substances with antimicrobial activity exhibit varying spectra of activity within the classes of microorganisms. Particular difficulties arise with respect to the test viruses of the DVV (German Organization for Combatting Viral Diseases). For some time, when no index of infectiousness or no definition of adequate inactivation for a specific disease-producing virus existed, aldehydes, phenols, alcohols and iodophors were considered virus inactivating substances in analogy to their bactericidal activity. However after the DVV established guidelines for the testing of specific model viruses, the a priori claims for virus inactivation could not be substantiated in most cases. Rather it turned out that for none of the known agents did the claim as general virucide, consistent with the guidelines of the DVV, prove right. Formaldehyde for example, which is known to be a broad spectrum disinfectant, does not fulfill the requirements for the inactivation of the $SV_{40}$-virus. The remaining agents either exhibit no inactivating activity against viruses or they inactivate only some in the viral spectrum, cf. Horn, Privora, Weuffen: "Handbook of Disinfection and Sterilization", Vol. III (1974), page 7 and J. Sporkenbach: "The Lack of Inactivation Activity of Some PVP-Iodine Compounds Toward Poliomyelitis and Adenoviruses", Hygiene & Medicine 5, 357 (1980). In light of this new knowledge, virology requires entirely different criteria than bacteriology for the evaluation of disinfectants. Therefore it appears worthy of effort to find a microbiocidal agent that is generally effective as a bactericide, fungicide and virucide.

Presently known microbiocidal agents are useful only for specific parameters. Aldehydes and phenols are mainly used for disinfection of hard surfaces and instruments, because these compounds, on the basis of skin compatibility, have restricted use as skin and hand disinfectants. Alcohols are not used in instrument disinfection due to their volatility and alcohol depletion by blood and serum. Iodophors are restricted to the disinfection of skin and hands due to their staining properties.

Until now, investigations to find an agent that embraces all fields of application of general microbiocidal and virucidal activities have led to the per-compound class of substances. Of the disinfectants in this class, only peracetic acid, a liquid, is in use. Disadvantages in the use of peracetic acid are its penetrating odor, its instability and explosive nature, as well as the fact that surfactants reduce its activity.

U.S. Pat. No. 3,873,696 discloses the antimicrobial activity of aqueous solutions containing potassium peroxymonosulfate in the form of its triple salt ($2KHSO_5.KHSO_4.K_2SO_4$) against certain bacteria and fungi.

SUMMARY OF THE INVENTION

Surprisingly, it has been discovered that salts of peroxymonosulfuric acid, commonly known as Caro's acid, exhibit virus inactivating properties similar to peracetic acid, but do not possess the undesirable properties of peracetic acid. The salts of Caro's acid, also designated as Caroates, are decidedly more active than the per-compounds, including percarboxylic acids. Moreover, the activity of the Caroates against the extraordinarily resistant poliovirus is better than that of other per-compounds.

Thus the invention provides a method for inactivating viruses which comprises contacting the locus of said viruses with an antivirally effective amount of a salt of peroxymonosulfuric acid.

The method of the invention is useful for inactivating viruses on virus-contaminated animate and inanimate surfaces.

DETAILED DESCRIPTION OF THE INVENTION

The peroxymonosulfuric acid salts which can be used in accordance with the invention are the water soluble salts such as ammonium salts, alkaline metal salts, e.g., sodium, potassium and lithium salts, and alkaline-earth metal salts, e.g., calcium and magnesium salts. A preferred salt is potassium peroxymonosulfate ($KHSO_5$) which in commercially available form is a mixture containing about 45 weight-percent potassium peroxymonosulfate, 30 weight-percent potassium sulfate ($K_2SO_4$) and 25 weight-percent potassium hydrogen sulfate ($KHSO_4$).

The peroxymonosulfate salts have the advantage that they decompose into non-toxic compounds during the oxidation reaction that takes place and therefore do not cause additional problems with respect to sewage disposal. Furthermore, compositions containing these salts have a lower chemical oxygen demand and a much lower COD-value compared to aldehydic and phenolic disinfectants, which is a further advantage with respect to sewage disposal.

The peroxymonosulfate salts can be formulated in aqueous media, e.g., as aqueous solutions, which may require further dilution with water prior to use depending on the particular use-concentration desired. Alternatively they can be formulated as dry compositions which are adapted for use in aqueous media by admixing with one or more suitable diluents, e.g., lactose, and, if desired, with adjuncts such as surfactants, sequestrants, buffers, etc.

In formulating the peroxymonosulfate salts either in aqueous media or as dry mixtures, it is preferable to add one or more surfactants, especially of the class of nonionic surfactants such as ethoxylated fatty alcohols and/or anionic surfactants such as alkyl sulfonates, alkylbenzene sulfonates, and fatty acid ethionates, which do not reduce the activity of the peroxymonosulfate salts. When employing a surfactant or mixture of surfactants, the amount to be used advantageously will be from about 0.5 to about 5 parts per part of the peroxymonosulfate salt, although lesser or greater amounts can be used.

In practicing the method of the invention, the peroxymonosulfate salts in aqueous media are applied to the surfaces to be disinfected in a use-dilution of at least about 0.05%, i.e., wherein the concentration of peroxymonosulfate salt in the aqueous medium is at least about 0.05%. The specific in-use dilution to be employed and the contact time with the virus-contaminated surface required to effect inactivation of the viruses will depend on a number of factors, such as the nature and degree of contamination of the surface to be treated, and can readily be determined by the skilled artisan.

The method of the invention is useful for treating inanimate surfaces including, for example, surfaces encountered in industrial, domestic and medical environments such as walls, floors and work surfaces, hospital utensils, surgical and dental instruments, etc., as well as animate surfaces, i.e., the skins of human and non-human animals, e.g., in the presurgical preparation of the skin in human and veterinary medicine.

The formulated peroxymonosulfate salts in appropriate use-dilution are applied to the surfaces to be treated by conventional means such as spraying, swabbing, rubbing and immersing.

The following are representative examples of compositions adapted for use in aqueous media in accordance with the invention:

| Composition TPH 5720 (Hand Disinfectant) | |
|---|---|
| Ingredient | Weight-Percent |
| Commercial Potassium Peroxymonosulfate[a] | 12.0[b] |
| Succinic Anhydride | 1.0 |
| Fatty Acid Ethionate Sodium Salt | 20.0 |
| Lactose | 62.0 |
| Sodium Alkane Sulfonate | 5.0 |
| | 100.0 |

[a]Contains about 45 wt % $KHSO_5$, 30 wt % $K_2SO_4$ and 25 wt % $KHSO_4$
[b]About 5.4% $KHSO_5$, 3.6% $K_2SO_4$ and 3.0% $KHSO_4$

| Composition TPH 574 | |
|---|---|
| Ingredient | Weight-Percent |
| Commercial Potassium Peroxymonosulfate[a] | 30.0[b] |
| Succinic Anhydride | 20.0 |
| Benzoic Acid | 10.0 |
| Sodium Dodecylbenzene Sulfonate | 5.0 |
| $C_{16-18}$ Alkanolethoxylate with 25 Ethylene Oxide Units | 1.0 |
| Disodium Pyrophosphate | 15.0 |
| Sodium Carbonate | 7.0 |
| Sodium Sulfate | 10.0 |
| Tetrasodium Ethylenediaminetetraacetate | 2.0 |
| | 100.0 |

[a]See footnote (a) for TPH 5720
[b]About 13.5% $KHSO_5$, 9.0% $K_2SO_4$ and 7.5% $KHSO_4$ The antiviral effects of the above compositions at different use-dilutions and of a solution of potassium peroxymonosulfate (commercial grade) alone against several representative viruses are recorded in Table 4 below.

The effects of potassium peroxymonosulfate and, for purpose of comparison also of a number of other per-compounds, against poliovirus are recorded in Tables 1 to 3 below.

Table 5 below compares the chemical oxygen demand of three disinfectants based respectively on potassium peroxymonosulfate, an aldehyde and a phenol. The values recorded in Table 5 were ascertained according to German standard methods.

The results recorded for potassium peroxymonosulfate in Tables 1 to 4 were based on the use of commercial potassium peroxymonosulfate as identified in footnote (a) for Composition TPH 5720 above. However the concentration given in each table was calculated on the basis of pure potassium peroxymonosulfate.

TABLE 1

Inactivating Activity Against Poliovirus (Exposure Time = 1 hour)

| Peracid | Conc. (%) | Reduction of Poliovirus Titer ($\log_{10}$) |
|---|---|---|
| Potassium Peroxymonosulfate | 0.05 | 6.5 |
| Peracetic Acid | 0.079 | 6.5 |

TABLE 2

Activity of Different Peracids Against Poliovirus After Exposure Time of 1 Hour (pH = 7.2)

| Peracid | Conc. (%) | Reduction of Poliovirus Titer ($\log_{10}$) |
|---|---|---|
| Potassium Peroxymonosulfate | 0.05 | 6.5 |
| Perbenzoic Acid | 0.1 | 6.5 |
| Persuccinic Acid | 0.1 | 3.5 |
| Percarbonate | 0.1 | 4.5 |

TABLE 3

Inactivation of Poliovirus by Different Per-Compounds

| Per-Compound | Conc. (Molarity) | Titer Reduction ($\log_{10}$) |
|---|---|---|
| Potassium Peroxymonosulfate | 0.0032 | 6.5 |
| Peracetic Acid | 0.0052 | 6.5 |
| Perbenzoic Acid | 0.015 | 5.0 |
| Monoperphthalic Acid | 0.012 | 3.0 |
| Peroxytrifluoroacetic Acid | 0.017 | 0 |
| tert-Butylhydroperoxide | 0.136 | 0 |

TABLE 4

Virus Inactivating Activity of Disinfectant Preparations Based on Potassium Peroxymonosulfate

| Preparation | Concentration | Serum Load | Virus Type | Titer Reduction ($\log_{10}$) | Time |
|---|---|---|---|---|---|
| Potassium Peroxymonosulfate | 0.05% | — | Poliovirus | 6 | 1h |
| TPH 5720 (Hand disinfection agent) | 20% | 3% | Poliovirus | 3.4 | 2 Min. |
| TPH 574 | 0.25% | — | Poliovirus | 8 | 1h |
| TPH 574 | 2% | 40% | Poliovirus | 3 | 1h |
| TPH 574 | 1% | — | Coxsackie Virus | 6 | 1h |
| TPH 574 | 3% | 40% | Coxsackie Virus | 4 | 4h |
| TPH 574 | 0.3% | — | $SV_{40}$-Virus | 7 | 1h |
| TPH 574 | 1% | 40% | $SV_{40}$-Virus | 4 | 1h |
| TPH 574 | 0.05% | — | Adenovirus | 5 | 1h |

TABLE 4-continued

| | Virus Inactivating Activity of Disinfectant Preparations Based on Potassium Peroxymonosulfate | | | | |
|---|---|---|---|---|---|
| Preparation | Concentration | Serum Load | Virus Type | Titer Reduction (log$_{10}$) | Time |
| TPH 574 | 0.5% | 40% | Adenovirus | 5 | 1h |

TABLE 5

| Chemical Oxygen Demand of Different Disinfectants | |
|---|---|
| Disinfectant (Conc. = 1.0%) | COD (mg O$_2$/l) |
| Based on salts of Caro's Acid | 415.9 |
| Based on aldehyde | 800 |
| Based on phenol | 1680 |

We claim:

1. A method for inactivating viruses which comprises contacting the viruses located on inanimate surfaces or on the skins of humans or non-human animals with an antivirally effective amount of a salt of peroxymonosulfuric acid selected from the group consisting of alkali metal salt, alkaline-earth metal salt and ammonium salt.

2. A method according to claim 1 wherein the salt of peroxymonosulfuric acid is an alkali metal salt.

3. A method according to claim 2 wherein the alkali metal salt of peroxymonosulfuric acid is potassium peroxymonosulfate.

4. A method for inactivating viruses which comprises contacting the viruses located on inanimate surfaces or on the skins of humans or non-human animals with an aqueous medium containing an antivirally effective amount of a salt of peroxymonosulfuric acid selected from the group consisting of alkali metal salt, alkaline-earth metal salt and ammonium salt.

5. A method according to claim 4 wherein the salt of peroxymonosulfuric acid is present in the aqueous medium in a concentration of at least about 0.05%.

6. A method according to claim 4, wherein the salt of peroxymonosulfuric acid is an alkali metal salt.

7. A method according to claim 6 wherein the salt of peroxymonosulfuric acid is potassium peroxymonosulfate.

* * * * *